United States Patent [19]

Yankner

[11] Patent Number: 5,137,873
[45] Date of Patent: Aug. 11, 1992

[54] SUBSTANCE P AND TACHYKININ AGONISTS FOR TREATMENT OF ALZHEIMER'S DISEASE

[75] Inventor: Bruce A. Yankner, Boston, Mass.

[73] Assignee: The Children's Medical Center Corporation, Boston, Mass.

[21] Appl. No.: 559,173

[22] Filed: Jul. 27, 1990

[51] Int. Cl.⁵ .................. A61K 37/42; A61K 37/02; C07K 7/06; C07K 7/22
[52] U.S. Cl. .................................. 514/15; 514/2; 530/327; 530/839
[58] Field of Search .................. 514/14, 15, 18; 530/327, 328, 331, 839; 436/811

[56] References Cited

U.S. PATENT DOCUMENTS

| | | | |
|---|---|---|---|
| 3,862,114 | 1/1975 | Scandrett | 530/327 |
| 4,059,693 | 11/1977 | Stewart | 424/177 |
| 4,728,605 | 3/1988 | Fudenberg et al. | 435/29 |
| 4,816,416 | 3/1989 | Averback | 436/166 |

OTHER PUBLICATIONS

W. A. Banks et al., *Brain Res. Bull.* 15: 287-292, 1985.
N. W. Kowall et al., *Proc. Natl. Acad. Sci.* 88: 7247-7251, Aug. 1991.
Yates et al., Peptides and Amines in Alzheimer-type dementia and Down's syndrome, in *Interdiscip. Top. Gerontol.* 19: 175-83 (1985).
Abstracted in *Chemical Abstracts* 104:521, Ab#66941e (1986).
Berkow, editor, *The Merck Manual*, 14th Ed., pp. 981, 2249-2250 (1982).
Crystal et al., *J. Neurochem.* 38:1781, 1982.
Bouras et al., *Alzheimer's Dis. Assoc. Disord.* 4:24, 1990.
Quigley et al., *Neuroscience* 41:41, 1991.
McKhann et al., *Neurology* 34:939-944, 1984.
Wisniewski et al., *Annals of Neurology* 17(3):278-282, 1985.
Lai et al., *Arch. Neurol.* 46:849-853, 1989.
Schellenberg et al., *Science* 241:1507-1510, 1988.
St. George-Hyslop et al., *Science* 235:885-90, 1987.
Snider et al., *Science*, vol. 251, p. 435, 1991.

Watson et al., *European Journal of Pharmacology*, vol. 87, p. 77, 1983.
Penn et al., *Neurology*, vol. 38, p. 219, 1980.
Davies et al., *Nature*, vol. 288, p. 279, 1980.
Armstrong and Terry, *Neuroscience Letters*, vol. 58, p. 139, 1985.
Harbaugh et al., *Neurosurgery*, vol. 15, p. 514, 1984.
Rossor et al., *Neuroscience Letters*, vol. 20, p. 373, 1980.
Beal et al., *Science* vol. 229, p. 289, 1985.
Cramer et al., *Journal of Neurology*, vol. 232, p. 346, 1985.
Yates et al., *Brain Research*, vol. 258, p. 45, 1983.
Bar-Shavit et al., *Biochemical and Biophysical Research Communications*, vol. 94, p. 1445, 1980.
Lavielle et al., *Biochemical Pharmacology*, vol. 37, p. 41, 1988.
Armstrong et al., *Neuroscience*, vol. 31, p. 663, 1989.
Marx, *Science*, vol. 253, p. 266, 1991.
Wirak et al., *Science*, vol. 253, p. 323, 1991.
Clevens and Beal, *Brain Research*, vol. 486, p. 387, 1989.
Beal and Mazurek, *Neurology*, vol. 37, p. 1205, 1987.
Stanfield et al., *Nature*, vol. 315, p. 498, 1985.
Murray et al., *Brain Research*, vol. 459, p. 76, 1988.
Ferrier, *Journal of Neurological Science*, vol. 62, p. 159, 1983.

(List continued on next page.)

*Primary Examiner*—Robert A. Wax
*Assistant Examiner*—Stephen Walsh

[57] ABSTRACT

Method for treatment of a disease in a patient characterized by accumulation of β-amyloid. The method includes identifying a patient potentially suffering from such a disease and contacting a neuron of the patient with a therapeutically effective amount of a tachykinin agonist such as substance P. Methods for screening for compounds useful for treating such a disease are also disclosed.

3 Claims, 4 Drawing Sheets

OTHER PUBLICATIONS

Robakis et al., *Proceedings of the National Academy of Sciences* USA, vol. 84, p. 419, 1987.
Kang et al., *Nature*, vol. 325, p. 733, 1987.
Sisodia et al., *Science*, vol. 248, p. 492, 1990.
Lee et al., *European Journal of Pharmacology*, vol. 130, p. 209, 1986.
Maggio, *Annual Review of Neuroscience*, vol. 11, p. 13, 1988.
Engberg et al., *Nature*, vol. 293, p. 222, 1981.
Mantyh et al., *Journal of Neuroscience*, vol. 9, p. 258, 1989.
Mai et al., *Neuroscience*, vol. 17, p. 709, 1986.
*The Wall Street Journal*, Aug. 15, 1991, p. B4.
*Biotechnology News Watch*, Aug. 5, 1991, pp. 2-4.
Yankner et al., 245 *Science* 417 (1989).
Whitson et al. 243 *Science* 1488 (1989).
Joachim et al. 341 *Nature* 226 (1989).

SUBSTANCE P AND TACHYKININ AGONISTS FOR TREATMENT OF ALZHEIMER'S DISEASE

This invention was made with funding from the U.S. government; the U.S. government has rights in the invention.

BACKGROUND OF THE INVENTION

This invention relates to treating diseases characterized by an undesirable buildup of β-amyloid protein.

β-amyloid protein is a 40-42 amino acid polypeptide which is the primary constituent of senile plaques and cerebrovascular deposits in Alzheimer's disease and Down's syndrome. Although this protein has been well characterized biochemically, its primary biological function and role in the pathogenesis of Alzheimer's disease is unknown.

The β-amyloid protein is encoded as part of a message that encodes a much larger precursor (the amyloid precursor protein, APP) which is neurotoxic to hippocampal neurons in culture. Yankner et al. 245 Science 417, 1989. Whitson et al., 243 Science 1488, 1989, however, describe a peptide homologous to β-amyloid which increases the survival of culture hippocampal neurons.

SUMMARY OF THE INVENTION

Applicant has discovered that the neurotoxic effects of β-amyloid may be mediated by inhibition of the tachykinin neuropeptide system, and that the deleterious effects of β-amyloid are selectively reversed by tachykinin neuropeptides (i.e., those peptides having sequence similarity to tachykinin as discussed below). Accordingly, in a first aspect, the invention features a method for treatment or prophylaxsis of neuronal accumulation of β-amyloid. The method includes identifying a patient potentially suffering from (or at risk for) such accumulation, and administering to the patient a therapeutically effective amount of a tachykinin agonist (as defined below).

In preferred embodiments, the tachykinin agonist comprises a polypeptide including a region homologous to (e.g., a sequence at least three and preferably five or more amino acids in length from) substance P, or physalaemin; more preferably the homologous region comprises the sequence GLM, in the C-terminal segment of the molecule; most preferably the tachykinin agonist is substance P or physalaemin. Another agonist having such a homologous region is neurokinin B. Other homologous derivatives of substance P or neurokinin B can be used.

In a second aspect, the invention features a method for identifying a tachykinin agonist useful for treatment of a disease (such as Alzheimer's disease or Down's syndrome) characterized by accumulation of β-amyloid. The method includes providing a potential tachykinin agonist, providing a β-amyloid-related polypeptide which is neurotoxic and determining whether the potential tachykinin agonist reduces the neurotoxic effect of the β amyloid polypeptide on a neuron. A reduction of β-amyloid-related neurotoxicity by the potential tachykinin agonist is indicative that the potential tachykinin agonist is useful for treatment of the disease.

While not wishing to be bound to any theory, we have also recognized that neurotoxic β-amyloid related polypeptides can also be neurotrophic (at earlier stages of neuronal differentiation) and that the preferred tachykinin agonists are those which overcome such a neurotrophic effect. Accordingly, preferred embodiments of the second aspect of the invention include determining whether a tachykinin agonist overcomes the neurotrophic effect of a β-amyloid protein; and preferred methods of treatment feature administering a tachykinin agonist that overcomes both the neurotrophic and neurotoxic effects of β-amyloid-related polypeptides.

Other preferred embodiments of the second aspect of the invention include administering the β-amyloid-related polypeptide to a neuron and measuring the neurotoxic or neurotrophic effect of the polypeptide on the neuron; administering the potential tachykinin agonist together with the β-amyloid-related polypeptide to a neuron and measuring the neurotoxic or neurotrophic effect of that combination of potential tachykinin agonist and polypeptide; and comparing the neurotrophic or neurotoxic effects of the polypeptide and the polypeptide together with the potential tachykinin agonist. While cultured neurons can be used in the second aspect of the invention, it is also possible to conduct in vivo determinations by intracerebral injection of potential tachykinin agonists into a mammal, e.g. rodents or primates.

Also we have recognized that the β-amyloid protein itself, without flanking APP sequences, is neurotoxic, and, indeed, polypeptides comprising residues 25-35 alone of the β-amyloid protein are neurotoxic. This recognition enables another aspect of the invention in which antagonists of such toxicity (tachykinins or other compounds) are identified, e.g. as useful for treating disease characterized by neuronal accumulation of β-amyloid. Specifically, a neurotoxic polypeptide comprising at least residues 25-35 of the β-amyloid protein (without APP sequences flanking the β-amyloid protein) is administered to a neuron in conjunction with the compound to be tested as a toxicity antagonists to determine whether the compound reduces the effect of the neurotoxicity (e.g. reduces death). This method has the advantage that the neurotoxin can be chemically synthesized rather than being produced by expression in an engineered cell, which, as a practical matter, is the method for producing larger amyloid-containing fragments of APP. See generally, PCT WO89/05138, hereby incorporated by reference. This aspect of the invention generally serves on a screening procedure for general therapeutics related to diseases characterized by excessive neuronal deposits of β-amyloid.

Other features and advantages of the invention will be apparent from the following description of the preferred embodiments, and from the claims.

DESCRIPTION OF THE PREFERRED EMBODIMENT

The drawings will first briefly be described.

DRAWINGS

TACHYKININ AGONISTS

Tachykinin agonists useful in this invention can be identified by any of a number of techniques, examples of which are provided below. In general, tachykinin agonists are those polypeptides which are able to overcome or reduce the neurotoxic or neurotropic effect of β-amyloid related polypeptides. Preferably, the method uses β-amyloid related polypeptides that have both effects, depending on the stage of neuronal differentiation. An example of such neurotoxic and neurotrophic effects is also provided below. The tachykinin agonists are able to compete with, (i.e., significantly reduce) or reverse, the neurotoxic and neurotrophic effects of the β-amyloid protein. In particular, they are able to reduce the neurotoxic and neurotrophic effects of a peptide that includes the 11 amino acid portion of the β-amyloid protein shown in FIG. 3, between amino acids 25 and 35 inclusive: GSNKGAIIGLM.

Potentially useful tachykinin agonists are those which have significant sequence similarity to either substance P or to physalaemin. That is, they have either conservative amino acid substitutions at one or more positions, or differ in a non-conservative manner at only one or two of the amino acids of these compounds. As discussed above, useful agonists can be readily identified from such homologous compounds by standard techniques, examples of which are provided below.

Tachykinin agonists of this invention inhibit at least 80% of the trophic and/or toxic effects of β-amyloid-related proteins, by the assay given below. These agonists are thought to interact at the receptor for substance P or the receptor for β amyloid within the brain; thus, tachykinin agonists which interact strongly with either of these receptors are particularly useful in this invention. Such agonists can again be identified by standard procedure by simply measuring their binding capacity for substance P receptors, for example, in a radioreceptor assay using substance P as a competitive binding agent for a substance P receptor. Specifically, substances containing the sequence GLM are preferred.

There follows an example of a method by which the neurotoxic or neurotrophic affect of potential tachykinin agonists can be measured. This example is provided to illustrate, not to limit the invention; those of ordinary skill in the art can readily determine other equivalent methods by which to measure the neurotoxic and neurotrophic effect of β-amyloid-related proteins, the reversal of such effect, or the inhibition of such effect by useful tachykinin agonists of this invention.

Figure 1A:
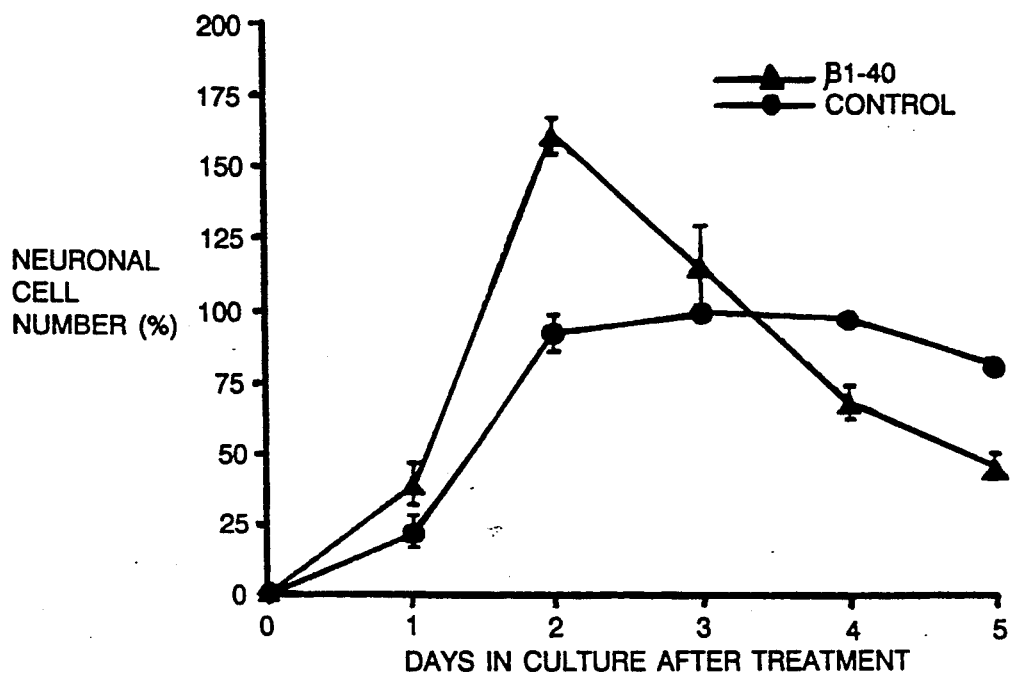
FIGS. 1A and 1B are graphical representations of the neurotrophic and neurotoxic effects of β-amyloid on hippocampal neurons.
Figure 3:
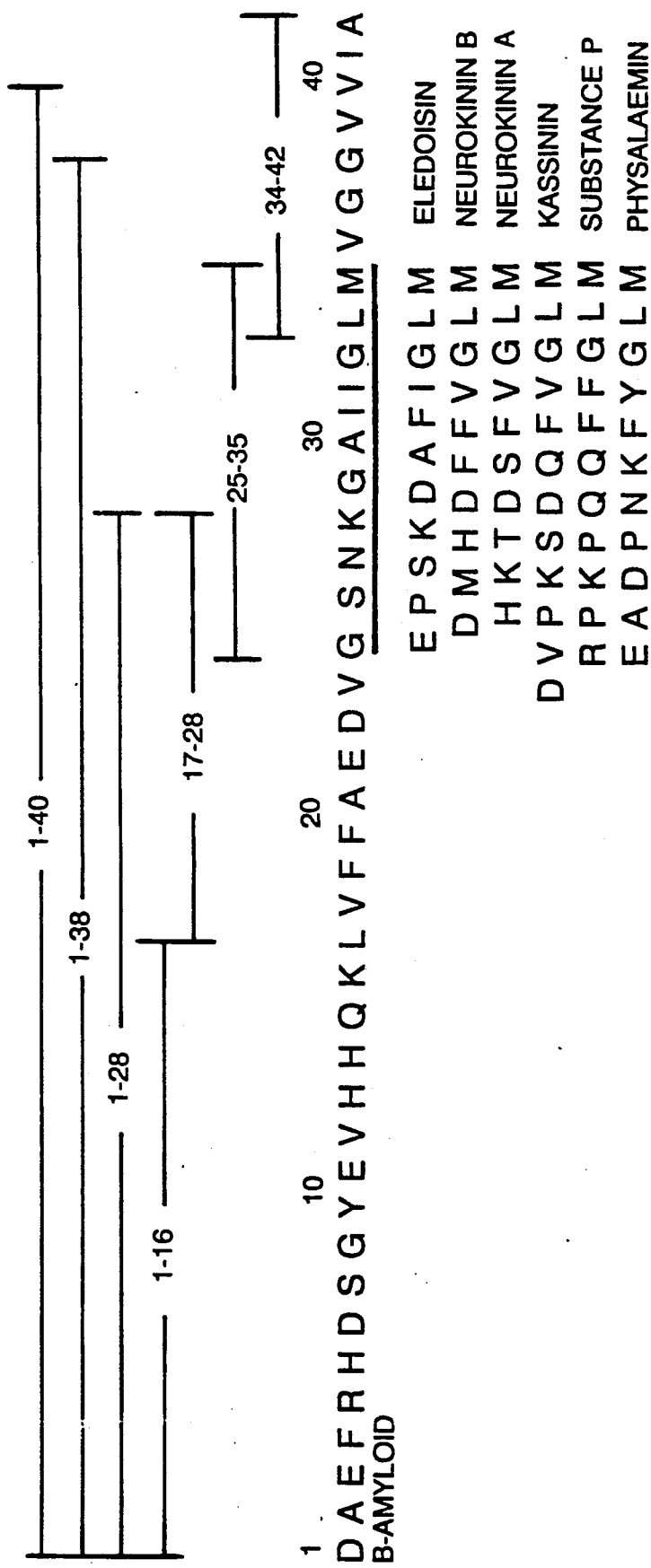
FIG. 3 is a representation of the amino acid sequence of β-amyloid and various tachykinin neuropeptides.

In this example, the polypeptide corresponding to the first 40 amino acids of β-amyloid (β1-40) was synthesized, purified, and the primary sequence confirmed (see FIG. 3). Referring to FIG. 1, the neurotrophic and neurotoxic effects of the β1-40 on hippocampal neurons was measured. In FIG. 1A, 20 μM β1-40 was added to hippocampal neurons at plating to result in an early increase (0-2 days) followed by a decrease (3-5 days) in neuronal cell number. Thus, addition of β1-40 to primary rat E18 hippocampal cultures at the time of subplating results in a significant increase in the number of pyramidal neurons during the first 2 days in culture. After 3 days in culture, however, there is a marked decline in neuronal cell number in cultures treated with β1-40, and by 4-5 days the number of pyramidal neurons in β1-40 treated cultures was significantly less than in control cultures.

Figure 1B:
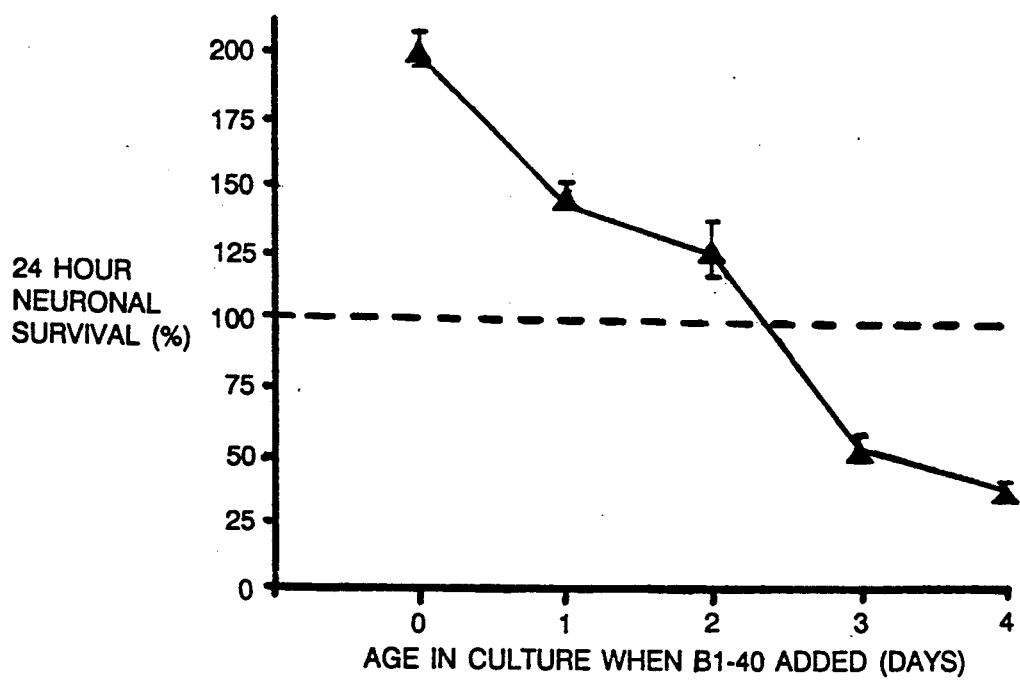

Referring to FIG. 1B, 20 μM β1-40 was added to hippocampal neurons of different ages in culture, and the number of neurons determined 24 hours later. β1-40 had a trophic effect on young neurons (values greater than 100% on days 0-2) and a toxic effect on older neurons (values less than 100% on days 3-5). The dashed line in the drawing indicates the transition from trophic to toxic response. Thus, when β1-40 is added at the time of plating (day 0) there is a significant increase in 24 hour neuronal survival relative to control values. This trophic effect progressively declines when β1-40 is added during the next two days in culture. If β1-40 is added to older cultures (3 days or later) there is an opposite effect, with a decline in 24 hour neuronal survival relative to controls. Control cultures remain viable and showed only a small change in neuronal survival using neurons up to 5 days old. These data show that β1-40 is neurotrophic when added during the early period of neuronal differentiation (days 0-2) and neurotoxic to older more differentiated neurons.

Figure 2:
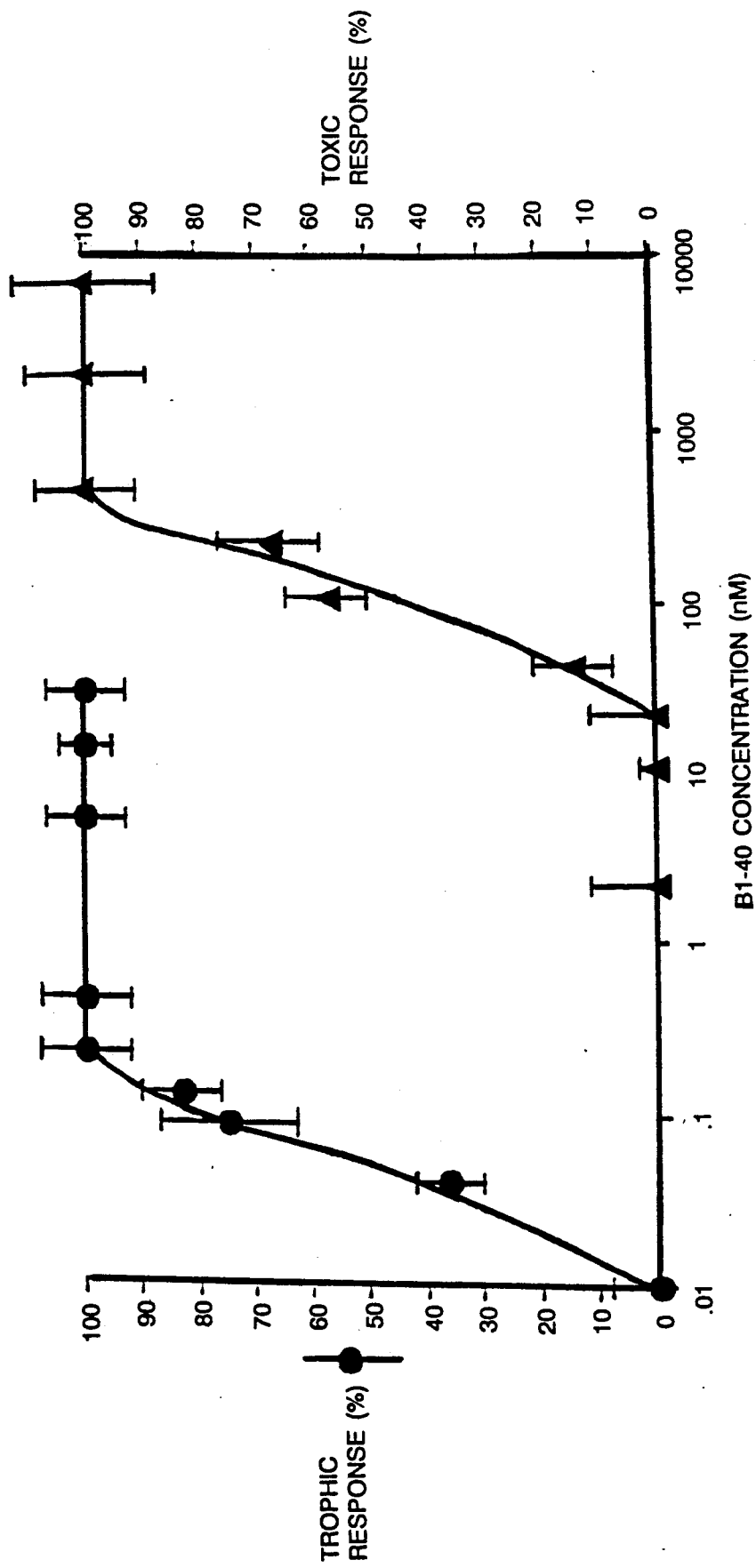
FIG. 2 is a graphical representation of the β-amyloid concentration dependence of the neurotrophic and neurotoxic responses.

Referring to FIG. 2, the neurotrophic and neurotoxic effects of β1-40 were separately assayed by adding β1-40 at day 0 and day 4, respectively, and determining 24 hour neuronal survival. The β1-40 concentration dependency of the neurotrophic and neurotoxic effects is shown in FIG. 2. The neurotoxic response requires about 1000-fold higher concentration of β1-40 than the neurotrophic response. The trophic response was determined by adding β1-40 at the indicated concentrations to neurons at the time of plating (day 0); the toxic response was determined by adding β1-40 to neurons at day 4 in culture. Values were normalized to the maximum β1-40-induced increase in neuronal cell number at day 0 (100% trophic response) and the maximum β1-40 induced decrease in neuronal cell number at day 4 (100% toxic response). The trophic response was detected at very low levels of β1-40 with an $EC_{50}$ of 0.06 nM. The toxic response required about 1000-fold higher concentrations of β1-40; it was first detected at 40 nM, with an $EC_{50}$ of about 100 nM.

The APP domain responsible for neurotrophic and neurotoxic effects was determined by assaying overlapping peptides spanning the entire β-amyloid precursor sequence (see FIG. 3 and table 1). The figures in the table were determined by treating hippocampal neurons at the time of cell plating, or at 4 days in culture, with the indicated peptides to measure the early trophic or late toxic responses, respectively, one day later. Values were normalized to the mean day 1 response (trophic response) and day 5 decrease (toxic response) in neuronal cell number observed for β1-40 (100% response). Peptide concentrations were at 20 μM except where indicated otherwise, and added directly to cell cultures. The values shown in the table are the means ± the standard error of the means using between 10 and 20 measurements for each peptide. The primary sequences of the designated β-amyloid sequences are shown in FIG. 3.

TABLE 1

| Peptide | % Trophic Response | % Toxic Response |
|---|---|---|
| β1-40 | 100 ± 6 | 100 ± 7 |
| β1-38 | 109 ± 10 | 97 ± 9 |
| β1-28 20 μM | 0 ± 5 | 0 ± 6 |
| β1-28 100 μM | 29 ± 10 | 55 ± 11 |
| β1-16 | 0 ± 8 | 0 ± 10 |

TABLE 1-continued

| Peptide | % Trophic Response | % Toxic Response |
|---|---|---|
| β17-28 | 0 ± 4 | 0 ± 8 |
| β25-35 | 100 ± 6 | 117 ± 12 |
| β34-42 | 0 ± 10 | 0 ± 7 |
| APP576-695 | 0 ± 4 | 0 ± 7 |
| Glucagon | 0 ± 3 | 0 ± 11 |
| Substance P | 16 ± 8 | 0 ± 7 |
| Physalaemin | 0 ± 4 | 0 ± 7 |
| Eledoisin | 0 ± 11 | 0 ± 6 |
| [D-Pro$^2$, D-Trp$^{7,9}$]-substance P | 125 ± 11 | 117 ± 13 |
| [D-Arg$^1$, D-Trp$^{7,9}$, Leu$^{11}$]-substance P (spantide) | 120 ± 8 | 118 ± 10 |
| Spantide + Substance P | 0 ± 8 | 26 ± 7 |

β1-38 elicited the same activity as β1-40. β1-28 showed some early neurotrophic and late neurotoxic activity, but was much less potent than β1-40 (Table 1). β1-16 and β17-28 showed no trophic or toxic activity at equimolar concentrations to β1-40. β17-28 showed similar activity to β1-28 at higher concentrations. The β25-35 peptide showed the same neurotrophic and neurotoxic activity as β1-40. β34-42 was inactive. A peptide corresponding to the carboxyterminal 20 amino acids of the amyloid precursor protein (APP676-695) and glucagon, a 28 amino acid peptide possessing β-pleated sheet structure similar to that of β-amyloid, were both inactive. Thus, the functional domain of β-amyloid required for the trophic and toxic effects is contained in the β25-35 sequence. The dose response relationship shown in FIG. 2 for β1-40 was also observed for β25-35.

β25-35 has 73% homology to eledoisin, including conservative changes, and 56% homology to the other tachykinins (FIG. 3). The region of greatest homology is in the carboxyterminal amino acids of the tachykinin sequence which is known to be required for high affinity tachykinin receptor binding and biological activity. Payan 40 Ann Rev. Med. 341, 1989.

Various tachykinins were tested for their effects on hippocampal neuronal survival. Exogenous substance P, eledoisin and physalaemin had no effect on early or late neuronal survival (Table 1). Tachykinin antagonists were also tested. The potent tachykinin antagonists [D-Pro$^2$, D-Trp$^{7,9}$]-substance P and [D-Arg$^1$, D-Trp$^{7,9}$, Leu$^{11}$]-substance P (spantide) showed significant early neurotrophic and late neurotoxic effects which could be reversed by the addition of substance P (Table 1). The effects of tachykinin antagonists closely mimicked those of β1-40 with respect to the time course and magnitude of changes in neuronal survival (Table 1).

Figure 4A:
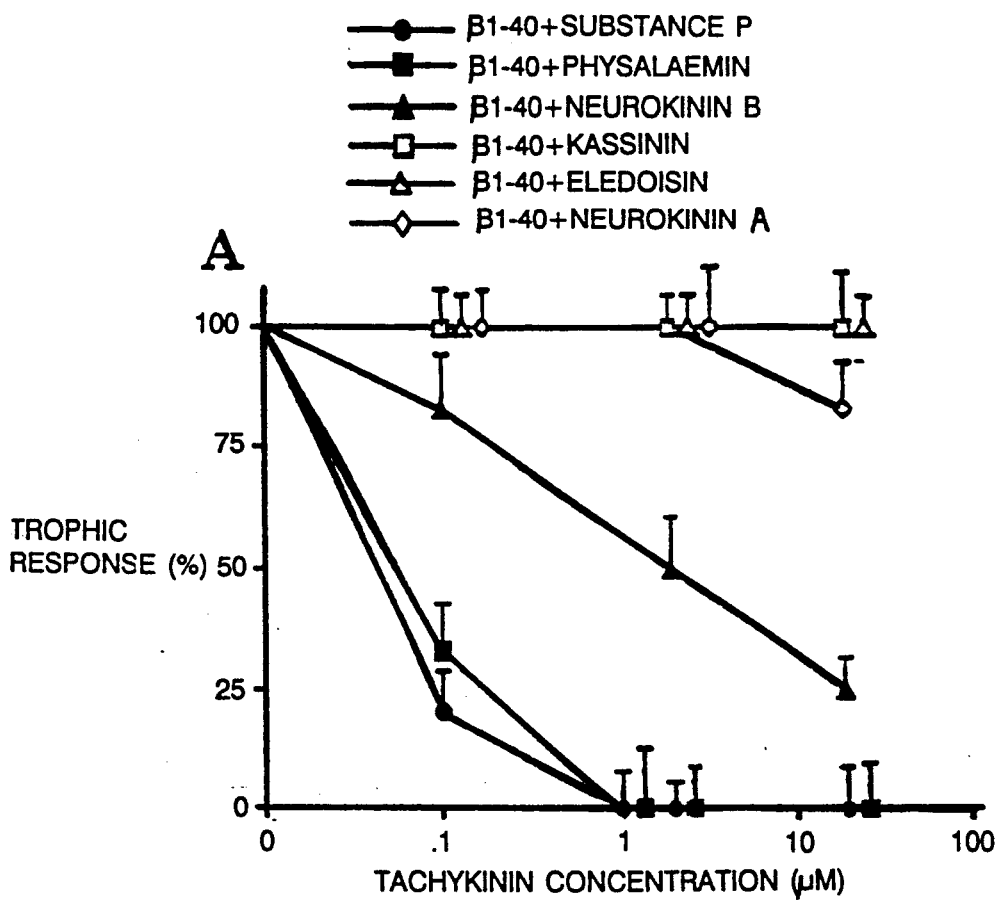
FIG. 4a and b are graphical representations of the effect of tachykinins on the trophic and toxic responses to β-amyloid.
Figure 4B:
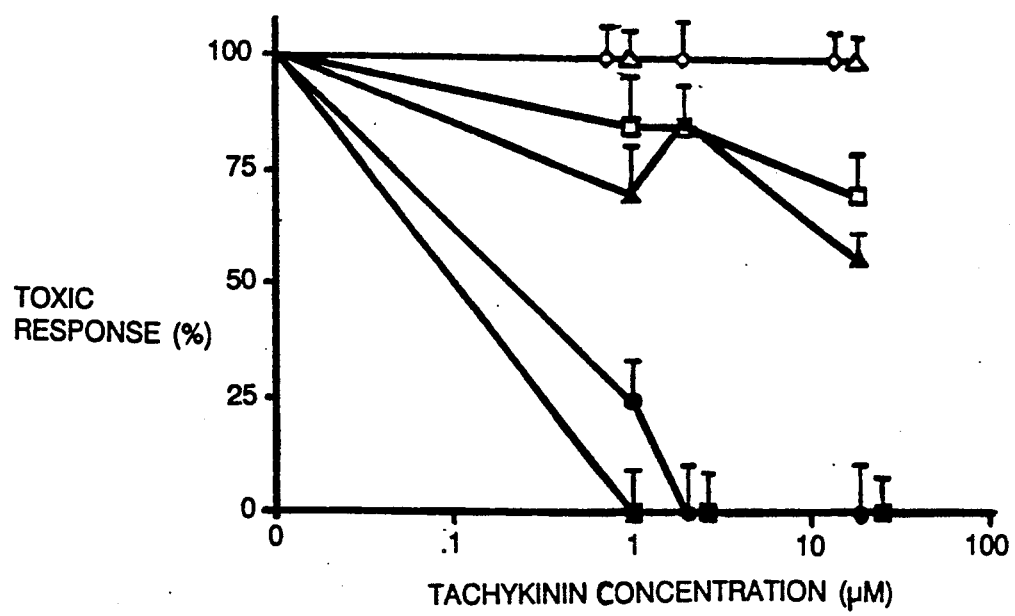

Since β-amyloid appears to act as a tachykinin antagonist the following experiment was performed to determine whether its activity could be reversed by tachykinin agonists. Tachykinin peptides were added along with β1-40 to hippocampal neurons at the time of plating to assay the trophic effect. Similarly, the toxic effect was assayed by adding these compounds after 4 days in culture. β1-40 was maintained at 20 μM at the time of cell plating and the trophic response determined 1 day later. The results of such experiments are shown in FIGS. 4A and 4B.

Substance P and physalaemin completely reversed (0%) the early trophic and late toxic responses to β1-40. Values were normalized to the mean day 0 trophic and day 4 toxic responses to β1-40 alone (100%); substance P and physalaemin acted in a dose dependent manner. Neurokinin B partially reversed the activity of β1-40, but was less potent than substance P and physalaemin. Neurokinin A, eledoisin and kassinin did not show significant effects in the concentration ranges tested. Thus, the effects of β-amyloid are selectively reversed by specific tachykinin neuropeptides.

An alternative method for identifying tachykinin agonists that reverse the neurotoxicity of β amyloid involves intracerebral injection of β amyloid alone or in combination with neurotrophic factors. The coinjection of the tachykinin agonist is tested for its ability to prevent an intracerebral neurotoxic response to β amyloid alone or in combination with neurotrophic factors. For example, test animals such as rats or monkeys can be injected and, after treatment, can be autopsied using antibodies specific for Alzheimer's Disease.

USE

Tachykinin agonists of this invention are useful for treatment of diseases characterized by accumulations of β-amyloid within a central nervous system. Such diseases include Alzheimer's disease and Down's syndrome. Patients who are at risk or who may be affected by such diseases can be generally identified by procedures well known to those of ordinary skill in the art, including external manifestations of such diseases, such as declined mental efficiency and shaking of limb extremities. They may also be characterized by detection of β-amyloid accumulation as described by Joachiun et al. 341 Nature 226, 1989. Once characterized, these patients can be treated by administering a tachykinin antagonist of this invention in an amount sufficient to reduce symptoms of the disease, or to inhibit progress of the disease. The amount of agonist to be administered will vary dependent upon the agonist, and can be determined by standard procedures. For any particular agonists, it is expected that a useful dose will be in the range of one nanomolar to one micromolar agonist, administered with a physiologically acceptable carrier directly to the central nervous system. Alternatively, the agonist may be administered orally or by intravenous, subcutaneous or intramuscular injection directly into the patients' tissues. The peptides may also be modified to enhance their absorption directly into the body, and thus may be administered topically.

Other embodiments are within the following claims.

I claim:

1. A method for ameliorating the neurotoxic effects associated with accumulation of β-amyloid proteins in a patient suffering from such effects, comprising administering to said patient a composition comprising a therapeutically effective amount of the tachykinin agonist substance P.

2. The method of claim 1 wherein said patient has Alzheimer's Disease or Alzheimer's Disease incident to Down's syndrome.

3. The method of claim 1 or 2 in which said composition is administered directly to the central nervous system of said patient.

* * * * *